(12) United States Patent
Lee et al.

(10) Patent No.: US 9,139,811 B2
(45) Date of Patent: Sep. 22, 2015

(54) COMPOSITION FOR SUSPENSION CULTURING OF STEM CELLS

(75) Inventors: Eun Ju Lee, Seoul (KR); Hyo Soo Kim, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 0 days.

(21) Appl. No.: 13/981,508

(22) PCT Filed: Dec. 27, 2011

(86) PCT No.: PCT/KR2011/010159
§ 371 (c)(1),
(2), (4) Date: Jul. 24, 2013

(87) PCT Pub. No.: WO2012/096461
PCT Pub. Date: Jul. 19, 2012

(65) Prior Publication Data
US 2014/0011275 A1  Jan. 9, 2014

(30) Foreign Application Priority Data

Jan. 14, 2011  (KR) .................. 10-2011-0004016

(51) Int. Cl.
| | | |
|---|---|---|
| C12N 5/071 | (2010.01) | |
| C12N 5/00 | (2006.01) | |
| C12N 5/0775 | (2010.01) | |
| A61K 31/4409 | (2006.01) | |

(52) U.S. Cl.
CPC .......... *C12N 5/0018* (2013.01); *A61K 31/4409* (2013.01); *C12N 5/0663* (2013.01); *C12N 2501/727* (2013.01)

(58) Field of Classification Search
None
See application file for complete search history.

(56) References Cited

U.S. PATENT DOCUMENTS

2009/0136459 A1* 5/2009 Wu et al. ............... 424/93.7

FOREIGN PATENT DOCUMENTS

JP   2008-99662 A   5/2008

OTHER PUBLICATIONS

Rosova et al., Stem Cells 2008; 26: 2173-2182.*
Song et al., Expert Opin. Biol. Ther. (2010), vol. 10, No. 3, pp. 309-319.*
Heng et al., Tissue and Cell, vol. 41 (2009), pp. 376-380.*
International Search Report of PCT/IB2011/001270 dated Feb. 23, 2012.
Watanabe et al., "A ROCK inhibitor permits survival of dissociated human embryonic stell cells" Nature Biotechnology, vol. 25, No. 6, pp. 681-686(May 27, 2007).
Emre et al., "The ROCK inhibitor Y-27632 improves recovery of human embryonic stem cells after fluorescence-activated cell sorting with multiple cell surface markers" PloS one, vol. 5, Issue 8, pp. 1-10; Aug. 2010.
Takehara et al., "Rho-associated kinase inhibitor Y-27632 promoters survival of cynomolgus monkey embryonic stem cells" Molecular Human Reproduction, vol. 14, No. 11, pp. 627-634(Oct. 21, 2008).
Lisa Mohamet et al; PLos ONE, vol. 5, Issue.9, Abrogation of E-Cadherin-Mediated Cellular Aggregation Allows Proliferation of Pluripotent Mouse Embryonic Stem Cells in Shake Flask Bioreactors; vol. 5, Sep. 2010).
Eagle, H.; Science; vol. 130:432 Amino Acid Metalobism in Mammalian Cell Cultures; Aug. 1959.
Stanner, C.P. et al., Nature New Biol. vol. 230:52 Two Types of Ribosome in Mouse-Hamster Hybrid Cells; Mar. 10, 1971.
Iscove, N.et al.; Journal of Experimental Medicine, vol. 147:923 Complete Replacement of Serum by Albumin, Transferrin, and Soybeam Lipid in Cultures of Lipopolysaccharide-Reactive B Lymphocytes; 1978.
Morgan et al., Proceedings of the Society of Experimental Biology & Medicine., vol. 73:1 "Nutrition of Animals Cells in Tissue Culture"; Jan. 1950.
Moore et al., Journal of Amer. Med. Assoc. vol. 199 No. 8; "Culutre of Normal Human Leukocytes" Feb. 1967.
Ham,Richard G; Proc. Natl. Acad. Sci. USA, vol. 53:288 Clonal Growth of Mammalian Cells in a Chemically Defined, Synthetic Medium; 1965.
Ham, Richard G. Experimental Cell Research; vol. 29:515 "An Improved Nutrient Solution for Diploid Chinese Hamster and Human Cell Lines" 1963.
Dulbecco's modification of Eagle's medium, Dulbecco, R. at al., Virology 8:396(1959).
Barnes, D. et al., Analytical Biochemistry, vol. 102:255; Methods for Growth of Cultured Cells in Serum-Free Medium; 1980.
Waymouth, C. J. Natl. Cancer Inst. 22:1003; rapid proliferation of sublines of nelt close 929 (Strain L) in a Simple Chemically Defined Medium (MB 752/1); Jan. 1959.
McCoy, T.A., et al., Proc. Soc. Exp. Biol. Med. vol. 100:115; "Amino Acid Requirements of the Novikoff Hepatoma In Vitro"; 1959.
Ham, R.G. et al., In Vitro; vol. 14:11; "Development of Improved Media and Culture Conditions for Clonal Growth of Normal Diploid Cells"; Jan. 1978.

* cited by examiner

*Primary Examiner* — Allison Fox
*Assistant Examiner* — Yvonne Pyla
(74) *Attorney, Agent, or Firm* — Lucas & Mercanti, LLP

(57) ABSTRACT

The present invention relates to a composition for suppressing the death of stem cells during suspension culturing, a composition for mass culturing of stem cells, and a method for suppressing cell death of stem cells during suspension culturing. The composition of the present invention can be usefully used for effective single suspension culturing of stem cells, particularly, mesenchymal stem cells, or used for mass suspension culturing under the circumstances in which cell aggregation does not occur.

4 Claims, 9 Drawing Sheets

After 24 hours

Suspension culture

Suspension culture + Y27632

E-cad

E-cad + Y27632

COMPOSITION FOR SUSPENSION CULTURING OF STEM CELLS

CROSS-REFERENCE TO RELATED APPLICATIONS

This application is a 371 of PCT/KR2011/010159, filed on Dec. 27, 2011, which claims the benefit of Korean Patent Application No. 10-2011-0004016, filed on Jan. 14, 2011, the contents of each of which are incorporated herein by reference.

TECHNICAL FIELD

The present invention relates to a composition for suspension culture of stem cells and a method for suspension culture of stem cells using the same.

BACKGROUND ART

As used herein, the term "stem cells" refers to undifferentiated cells that can differentiate into various types of cells constituting tissues of an organism and that can be obtained from respective tissues of an embryo, a fetus and an adult body. Stem cells differentiate into specific cells by a differentiation stimulus (environment) and are capable of proliferation (expansion) by producing identical cells through cell division (self-renewal), unlike differentiated cells whose cell division is arrested. Also, stem cells can differentiate into different cells under different environments or differentiation stimuli, and thus have plasticity in differentiation.

Stem cells are largely divided into two categories: embryonic stem cells (ES cells) which are obtainable from an embryo, can differentiate into all cell types and are totipotent and pluripotent; and multipotent adult stem cells obtainable from each tissue. Embryonic stem cells are undifferentiated cells capable of indefinite proliferation, can differentiate into all cell types, and can be inherited to the next generation through the preparation of germ cells, unlike adult stem cells. Despite such advantages, embryonic stem cells are difficult to use as cell therapeutic agents, due to carcinogenesis, immune rejection, and ethical and legal restrictions.

In recent years, mesenchymal stem cells have been proposed as an alternative to overcome such problems. Mesenchymal stem cells are multipotent cells capable of differentiating into adipocytes, osteocytes, chondrocytes, myocytes, neurocytes and cardiomyocytes and were reported to have the function of regulating immune responses.

The minimal number of cells required in cell therapy or regenerative medicine is about $1 \times 10^9$, which further increases when considering the cells required in a process of establishing culture conditions and standards. In the case of conventional mesenchymal stem cells derived from various origins, at least 10 passages of in vitro experiment are required to obtain such an amount of cells. In such a case, the cells would become aged and modified, which would make them inadequate for use in therapy. This is one of the problems to be solved in current systems for culture of mesenchymal stem cells. In order to use mesenchymal stem cells as cell therapeutic agents, a novel mass production method capable of solving this problem is required.

Mesenchymal stem cells are adhesion-dependent cells and aggregate in a suspension culture process. The in vivo activity of the cells can be increased by such aggregation, but when mesenchymal stem cells are applied to suspension culture for mass production or applied to in vivo culture in the form of single cells, it is required to prevent apoptosis. Suspension culture of single cells is most suitable for highly efficient production of large amounts of mesenchymal stem cells, and thus there need to develop a method for efficient culture of large amounts of mesenchymal stem cells is by developing a method that prevents the death of cells, which do not aggregate, and maintains the activity of cultured cells.

Throughout the specification, a number of publications and patent documents are referred to and cited. The disclosure of the cited publications and patent documents is incorporated herein by reference in its entirety to more clearly describe the state of the related art and the present disclosure.

DETAILED DESCRIPTION OF THE INVENTION

Technical Problem

The present inventors have made extensive efforts at developing an efficient mass production method that increases the viability of mesenchymal stem cells and maintains the activity of mesenchymal stem cells. As a result, the present inventors have found that, when an ROCK inhibitor is added during the suspension culture of mesenchymal stem cells, the apoptosis of cells that do not aggregate can be inhibited while the suspension culture or single-cell culture of large amounts of mesenchymal stem cells is possible, thereby completing the present invention.

Therefore, it is an object of the present invention to provide a composition for inhibiting apoptosis of stem cells during suspension culture.

Another object of the present invention is to provide a composition for culturing large amounts of stem cells.

Still another object of the present invention is to provide a method for inhibiting apoptosis of stem cells during suspension culture.

Other objects and advantages of the present invention will be more clearly understood by the following detailed description, the appended claims and the accompanying drawings.

Technical Solution

In accordance with one aspect of the present invention, there is provided a composition for inhibiting apoptosis of stem cells during suspension culture, the composition comprising a Rho-associated kinase (ROCK) inhibitor as an active ingredient.

The present inventors have made extensive efforts at developing an efficient mass production method that increases the viability of mesenchymal stem cells and maintains the activity of mesenchymal stem cells. As a result, the present inventors have found that, when an ROCK inhibitor is added during the suspension culture of mesenchymal stem cells, the apoptosis of cells that do not aggregate can be inhibited while the suspension culture or single-cell culture of large amounts of mesenchymal stem cells is possible.

The composition of the present invention is expressed as "composition for inhibiting apoptosis of stem cells during suspension culture". In addition, the composition of the present invention can also be expressed as "composition for culturing individual non-aggregated stem cells".

As used herein, the term "ROCK (Rho-associated kinase)" refers to a kinase that belongs to the AGC (PKA/PKG/PKC) family of serine-threonine kinases and that occurs in mammals (humans, rats, mice, etc.), zebrafish, *Xenopus*, invertebrates (*C. elegans*, Mosquitoes, *Drosophilas*, etc.) and chicken. Mammalian ROCK consists of a kinase domain, a coiled-coil region and a Pleckstrin homology (PH) domain, which reduces the kinase activity of ROCKs by an autoinhibitory intramolecular fold if RhoA-GTP is not present. Human ROCK has a molecular weight of 158 kDa and is a major downstream effector protein of the small GTPase RhoA. The term "ROCK (Rho-associated kinase) inhibitor" includes Y-27632(trans-4-[(1R)-1-Aminoethyl]-N-4-pyridinyl-cyclohexanecarboxamide, 2HCl), H-1152[(S)-(+)-(2-methyl-5-isoquinolinyl)sulfonylhomopiperazine, 2HCl], HA-1077[(5 isoquinolinesulfonyl)homopiperazine, 2HCl], and ROCK inhibitor II [N-(4-pyridyl)-N'-(2,4,6-trichlorophenyl urea], but is not limited thereto and includes all substances known in the art to inhibit the activity of ROCK.

As used herein, the term "stem cells" refers to undifferentiated cells that can differentiate into various types of cells constituting the tissue of an organism and that can regenerate unlimitedly to form specialized cells of tissues and organs. A stem cell is a developable multipotent or pluripotent cell. A stem cell can be divided into two daughter stem cells or into one daughter stem cell and one transit cell and is then proliferated into a mature and complete type of cell. Preferably, the stem cells in the present invention are mesenchymal stem cells.

As used herein, the term "mesenchymal stem cells" refers to multipotent stem cells capable of differentiating into adipocytes, osteocytes, chondrocytes, myocytes, neurocytes and cardiomyocytes. Mesenchymal stem cells are identified by a swirling shape and the expression levels of cell surface markers such as CD73(+), CD105(+), CD34(−) and CD45(−).

As used herein, the term "suspension culture" refers to a culture in which the cells to be cultured are suspended in a medium without adhering to a substrate or the like. Adhesion-dependent mesenchymal stem cells aggregate during suspension culture, and cells, which do not aggregate and are suspended alone, undergo apoptosis. Thus, when stem cells are required to be cultured in large amounts by suspension culture or to be cultured alone in vivo, it is required to inhibit apoptosis of the stem cells in order to guarantee high cell viability. According to the present invention, the ROCK inhibitor inhibits apoptosis of stem cells during suspension culture to increase the number of cells and maintain the activity of cells, thereby greatly increasing the efficiency of suspension culture.

According to a preferred embodiment of the present invention, stem cells in the present invention are cells that are cultured without aggregation during suspension culture. According to the present invention, the ROCK inhibitor can increase cell aggregation while inhibiting apoptosis of mesenchymal stem cells that do aggregate during suspension culture. Thus, the ROCK inhibitor greatly increases the yield of stem cells in suspension culture by increasing the viability of adhesion-dependent stem cells.

According to a preferred embodiment of the present invention, the ROCK inhibitor is a compound represented by the following formula 1:

Formula 1

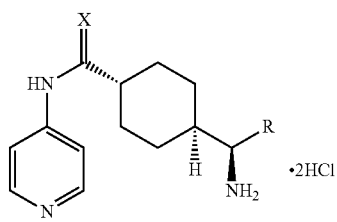

wherein X is oxygen or sulfur, and R is a $C_1$-$C_3$ alkyl group. More preferably, X is oxygen, and R is a methyl group.

The compound of formula 1 in which X is oxygen and R is a methyl group is Y-27632 (trans-4-[(1R)-1-Aminoethyl]-N-4-pyridinyl-cyclohexanecarboxamide, 2HCl). Y-27632 was reported to function to form floating aggregates during suspension culture of embryonic stem cells and increase cell viability, but the function of Y-27632 to apoptosis of isolated mesenchymal stem cells during suspension culture is not yet known.

According to a preferred embodiment of the present invention, stem cells in the present invention are human mesenchymal stem cells.

According to a preferred embodiment of the present invention, the composition of the present invention further comprises an antioxidant.

As used herein, the term "antioxidant" refers to a molecule that inhibits the oxidation of other molecules. Oxidation reactions produce free radicals which start chain reactions that damage cells. Antioxidants are oxidized by themselves to remove free radical intermediates so as to terminate such chain reactions. Thus, the antioxidants are frequently reducing agents. The antioxidant that is used in the present invention is any antioxidant known in the art to be used in cell culture. Preferably, the antioxidant is selected from the group consisting of glutathione, cysteine, cysteamine, ubiquinol and bME (beta-mercaptoethanol). Most preferably, the antioxidant that is used in the present invention is bME (beta-mercaptoethanol).

According to the present invention, it was found that, when bME was added together with the ROCK inhibitor during single-cell suspension culture of stem cells, the viability of the stem cells greatly increased. Thus, the additional use of bME in the culturing composition can greatly increase the efficiency with which stem cells are cultured in single-cell suspension culture or under a condition in which no cell aggregation occurs.

In accordance with another aspect, the present invention provides a method for inhibiting apoptosis of stem cells during suspension culture, the method comprising a step of subjecting stem cells to suspension culture in the presence of an ROCK (Rho-associated kinase) inhibitor.

In accordance with still another aspect, the present invention provides a composition for culturing large amounts of stem cells, the composition comprising, as active ingredients, an E-cadherin blocker, an ROCK (Rho-associated kinase) inhibitor and an antioxidant.

As used herein, the term "E-cadherin blocker" refers to any substance that inhibits the activity of the $Ca^{2+}$-dependent cell adhesion factor E-cadherin. Examples of the E-cadherin blocker include, but are not limited to, human E-cadherin monoclonal antibodies (e.g., HECD-1 and SHE78-7), and nucleic acid molecules (e.g., shRNA, siRNA, miRNA, ribozyme, peptide nucleic acid (PNA) or an antisense oligonucleotide). In addition, the E-cadherin blocker is any substance known in the art to inhibit the activity of E-cadherin. Preferably, the E-cadherin blocker that is used in the present invention is an E-cadherin antibody that is produced by recognizing E-cadherin as an antigen, and more preferably, the E-cadherin blocker is an E-cadherin antibody that is produced by recognizing the extracellular portion of E-cadherin as an antigen.

As used herein, the term "inhibition of expression" refers to modification in the nucleotide sequence of a target gene, which results in a decrease in the function of the target gene.

Preferably, the term means that the expression of the target gene cannot be detected or reduced to an insignificant level due to the modification.

In previous studies, the present inventors found that E-cadherin is the major cause of aggregation of mesenchymal stem cells, and when the expression of E-cadherin is inhibited, dissociated cells undergo apoptosis during suspension culture. Thus, when the E-cadherin blocker and the ROCK blocker are added together, no cell aggregation will occur while the cell viability and activity will not be influenced, and thus the production of large amounts of stem cells will be possible and the culture of single cells in vivo can also be efficiently performed.

According to a preferred embodiment of the present invention, the ROCK inhibitor that is used in the present invention is a compound represented by the following formula 1:

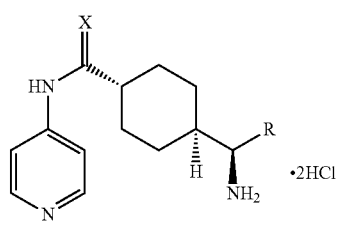

Formula 1 wherein X is oxygen or sulfur, and R is a $C_1$-$C_3$ alkyl group. More preferably, X is oxygen, and R is a methyl group. The ROCK inhibitor that is used in the present invention is as described above, and thus the repeated description thereof is omitted.

According to a preferred embodiment of the present invention, stem cells in the present invention are human mesenchymal stem cells.

The method of the present invention is expressed as "method for inhibiting apoptosis of stem cells during suspension culture". In addition, the composition of the present invention may also be expressed as "method for suspension culture of stem cells".

A medium for suspension culture of stem cells, which is used in the present invention, may be any medium that is generally used in the culture of stem cells. Examples of the medium that may be used in the present invention include Eagles's MEM (Eagle's minimum essential medium, Eagle, H. Science 130:432(1959)), α-MEM (Stanner, C. P. et al., Nat. New Biol. 230:52(1971)), Iscove's MEM (Iscove, N. et al., J. Exp. Med. 147:923(1978)), 199 medium (Morgan et al., Proc. Soc. Exp. Bio. Med., 73:1(1950)), CMRL 1066, RPMI 1640 (Moore et al., J. Amer. Med. Assoc. 199:519(1967)), F12 (Ham, Proc. Natl. Acad. Sci. USA 53:288(1965)), F10 (Ham, R. G. Exp. Cell Res. 29:515(1963)), DMEM (Dulbecco's modification of Eagle's medium, Dulbecco, R. et al., Virology 8:396(1959)), a DMEM/F12 mixture (Barnes, D. et al., Anal. Biochem. 102:255(1980)), Way-mouth's MB752/1 (Waymouth, C. J. Natl. Cancer Inst. 22:1003(1959)), McCoy's 5A (McCoy, T. A., et al., Proc. Soc. Exp. Biol. Med. 100:115(1959)), and MCDB series (Ham, R. G. et al., In Vitro 14:11(1978)).

In order to culture cells in a suspended state, it is preferable to add SR (serum replacement) to a medium or perform the culture process performed using a low-adherent culture dish or a bioreactor, but the scope of the present invention is not limited thereto, and various suspension culture methods that are used in the art may be used in the present invention.

According to a preferred embodiment of the present invention, the composition of the present invention further comprises an antioxidant.

According to a preferred embodiment of the present invention, the antioxidant that is used in the present invention is selected from the group consisting of glutathione, cysteine, cysteamine, ubiquinol and bME (beta-mercaptoethanol). Most preferably, the antioxidant that is used in the present invention is bME (beta-mercaptoethanol).

The antioxidant that is used in the present invention is as described above, and thus the repeated description thereof is omitted.

In accordance with another aspect, the present invention provides a method for inhibiting apoptosis of stem cells during suspension culture, the method comprising a step of subjecting stem cells to suspension culture in the presence of an ROCK inhibitor under a condition in which aggregation of the stem cells is inhibited.

The ROCK inhibitor that is used in the present invention and the method for culturing stem cells are as described above, and thus the repeated description thereof is omitted.

According to a preferred embodiment of the present invention, the condition in which aggregation of stem cells is inhibited is formed by adding an E-cadherin blocker.

According to a preferred embodiment of the present invention, the condition in which aggregation of stem cells is inhibited is formed by making an anoxic condition.

As used herein, the term "anoxic condition" refers to a condition in which the oxygen concentration of air in a culture environment is reduced. Preferably, the oxygen concentration of air in a culture environment is 0-3 ppm, and more preferably 0-1 ppm. The anoxic condition can be formed by various methods known in the art, and a variety of commercially available systems for anaerobic microbial culture may be used in the present invention. The present inventors have found that, when mesenchymal stem cells are subjected to suspension culture under an anoxic anaerobic condition, the cells are suspended as single cells without aggregation. Apoptosis resulting from single-cell suspension caused by the anoxic anaerobic condition can be prevented using the ROCK inhibitor, and thus single-cell culture or suspension mass culture can be efficiently performed.

According to a preferred embodiment of the present invention, the ROCK inhibitor that is used in the present invention is a compound represented by the following formula 1:

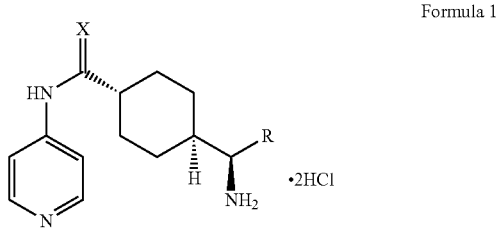

Formula 1 wherein X is oxygen or sulfur, and R is a $C_1$-$C_3$ alkyl group. More preferably, X is oxygen, and R is a methyl group. The ROCK inhibitor that is used in the present invention is as described above, and thus the repeated description thereof is omitted.

According to a preferred embodiment of the present invention, stem cells in the present invention are human mesenchymal stem cells.

Advantageous Effect

The features and advantages of the present invention are summarized as follows:

(a) The present invention provides a composition for inhibiting apoptosis of stem cells during suspension culture, a composition for culturing large amounts of stem cells, and a method for inhibiting apoptosis of stem cells during suspension culture.

(b) The present invention can be efficiently used for the single-cell suspension culture or suspension mass culture of stem cells, particularly mesenchymal stem cells, under a condition in which no cell aggregation occurs.

BRIEF DESCRIPTION OF THE DRAWINGS

FIG. 8 is a set of photographs showing the results of comparing the activity of suspension-cultured stem cells between treatment and non-treatment with Y27632 and bME at 24 hours after forming an aerobic condition using an anoxic pack.

MODE FOR CARRYING OUT THE INVENTION

Figure 1:
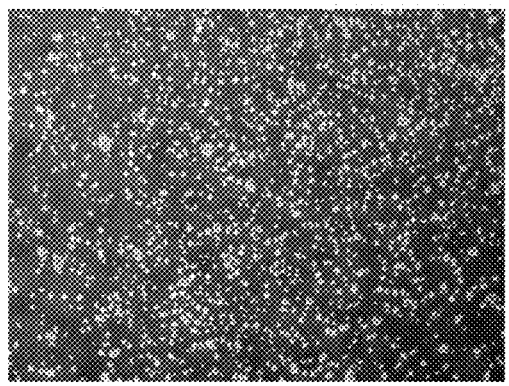
FIG. 1 is a set of photographs (40× magnification) showing the results of trypan blue staining of aggregated cells after 24 hours of culture of Y27632-untreated control cells and Y27632-treated cells.
Figure 1:
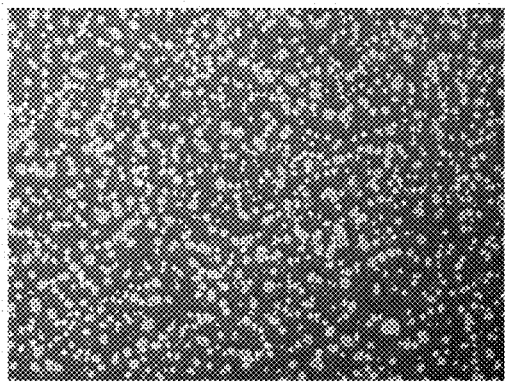

Hereinafter, the present invention will be described in further detail with reference to examples. It will be obvious to those skilled in the art that these examples are for illustrative purposes only and are not intended to limit the scope of the present invention.

EXAMPLES

Test Methods

Culture of Human Mesenchymal Stem Cells (BM-MSC) and Cell Counting

Human mesenchymal stem cells (Lonza, Switzerland) were cultured in 10% FBS-containing α-MEM medium such that no contact inhibition occurred. When a confluence of about 80% was reached, the medium was removed by suction for cell counting, and the cells were washed with PBS (calcium-free and magnesium-free). Then, the cells were treated with 0.25% trypsin/EDTA and allowed to stand in a $CO_2$ incubator at 37° C. for 30 seconds. The cells that dropped into the tube were collected, and the cells remaining in the dish were completely collected with 10% FBS-containing α-MEM, and the collected cells were centrifuged at 1500 rpm for 5 minutes. The supernatant medium was removed by suction, and the precipitated cells were suspended in 5 ml of EB medium (80% DMEM/F12 80%+20% serum replacement) and then centrifuged at 1500 rpm for 5 minutes. Then, the cells were suspended in 10 ml of medium (containing or not containing 20 μM Y27632) in a 100 Φ Petri dish at a density of $2.0 \times 10^6$ cells. After 24 hours, the aggregated cells were stained with trypan blue, and then counted with an automated cell counter (Invitrogen).

Western Blotting

In order to measure a change in the expression of an anti-apoptosis factor in a cell sample, the expression level of BCL-XL was measured at the protein level. In addition, the cells were collected after suspension culture for 6 hours, and the degree of phosphorylation of ERK which is involved in the activity of the cells was evaluated. Specifically, the cells were lysed with a reducing agent [Lysis PreMix (4° C. stock)+NaF (10M, ×100)+orthovanadate (200 mM, ×200)+proteinase inhibitor cocktail (1 tablet/10 ml)], and then electrophoresed on SDS-polyacrylamide gel. Then, the cells were transferred to a PVDF transfer membrane (Millipore), after which a change in the expression of the protein was examined by a primary antigen-antibody reaction using BCL-xl (Santa Cruz Biotechnology) and a secondary antigen-antibody reaction using anti-rabbit IgG and anti-mouse IgG.

HGF ELISA

In vivo conditions in which treatment of cells is required are mostly ischemic anoxic anaerobic conditions in which the cells are injured or broken, and one of major factors in the conditions is HGF (hepatocyte growth factor). Thus, in order to examine the expression level of the hepatocyte growth factor HGF, the supernatant was collected from the cell sample and analyzed by ELISA (enzyme-linked immunosorbent assay) using a HGF-specific antibody according to the manufacturer's protocol.

Culture of human mesenchymal stem cells under anoxic condition and cell counting Human mesenchymal stem cells were cultured in 10% FBS-containing α-MEM medium such that no contact inhibition occurred. When a confluence of about 80% was reached, the medium was removed by suction for cell counting, and the cells were washed with PBS (calcium-free and magnesium-free). Then, the cells were treated with 0.25% trypsin/EDTA and allowed to stand in a $CO_2$ incubator at 37° C. for 30 seconds. The cells that dropped into the tube were collected, and the cells remaining in the dish were completely collected with 10% FBS-containing α-MEM, and the collected cells were centrifuged at 2000 rpm for 5 minutes. The supernatant medium was removed by suction, and the precipitated cells were suspended in 5 ml of EB medium (80% DMEM/F12 80%+20% serum replacement) and then centrifuged at 1500 rpm for 5 minutes.

Then, the cells were suspended in 10 ml of medium (containing or not containing 20 μM Y27632) in a 100 Φ Petri dish at a density of $2.0 \times 10^6$ cells. Then, the cells were placed in an anoxic pack (BD Science) to induce an anoxic anaerobic condition. After 24 hours, the aggregated cells were stained with trypan blue, and then counted with an automated cell counter (Invitrogen).

Induction of single-cell culture of human mesenchymal stem cells (BM-MSC) by suspension Human mesenchymal stem cells were cultured in 10% FBS-containing α-MEM medium such that no contact inhibition occurred. When a confluence of about 80% was reached, the medium was removed by suction for cell counting, and the cells were washed with PBS (calcium-free and magnesium-free). Then, the cells were treated with 0.25% trypsin/EDTA and allowed to stand in a $CO_2$ incubator at 37° C. for 30 seconds. The cells that dropped into the tube were collected, and the cells remaining in the dish were completely collected with 10% FBS-containing α-MEM, and the collected cells were centrifuged at 1500 rpm for 5 minutes. The supernatant medium was removed by suction, and the precipitated cells were suspended in 5 ml of EB medium (80% DMEM/F12 80%+20% serum replacement) and then centrifuged at 1500 rpm for 5 minutes. Then, the cells were suspended in 10 ml of medium (containing or not containing 20 μM Y27632 and containing or not containing 1.43 μM beta-mercaptoethanol) in a 100 Φ Petri dish at a density of $2.0 \times 10^6$ cells.

The present inventors have found that the aggregation of human mesenchymal stem cells during suspension culture is inhibited under an apoxic/anaerobic condition. Based on this finding, for suspension culture without cell aggregation, the Petri dish was placed in an anoxic pack (BD Science) to induce an anoxic/anaerobic condition and was incubated at 37° C. for 24 hours, followed by observation.

In addition, the present inventors have found that the major cause of aggregation of human mesenchymal stem cells during suspension culture is E-cadherin. In order to use E-cadherin to induce single-cell culture during suspension culture, the cells were treated with an E-cadherin blocker to inhibit the induction of cell aggregation during suspension culture. Specifically, human mesenchymal stem cells were cultured in 10% FBS-containing α-MEM medium such that no contact inhibition occurred. When a confluence of about 80% was reached, the medium was removed by suction for cell counting, and the cells were washed with PBS (calcium-free and magnesium-free). Then, the cells were treated with 0.25% trypsin/EDTA and allowed to stand in a $CO_2$ incubator at 37° C. for 30 seconds. The cells that dropped into the tube were collected, and the cells remaining in the dish were completely collected with 10% FBS-containing α-MEM, and the collected cells were centrifuged at 1500 rpm for 5 minutes. The supernatant medium was removed by suction, and the precipitated cells were suspended in 5 ml of EB medium (80% DMEM/F12 80%+20% serum replacement) and then centrifuged at 1500 rpm for 5 minutes. Then, the cells were suspended in 10 ml of medium (containing 12/ml E-cadherin blocker (E-cadherin neutralizing antibody; clone DECMA-1, Abcam) and containing or not containing 20 μM Y27632) in a 100 Φ Petri dish at a density of $2.0 \times 10^6$ cells.

Test Results

Measurement of Viability of Human Mesenchymal Stem Cells (UCB-MSC and BM-MSC)

Figure 2:
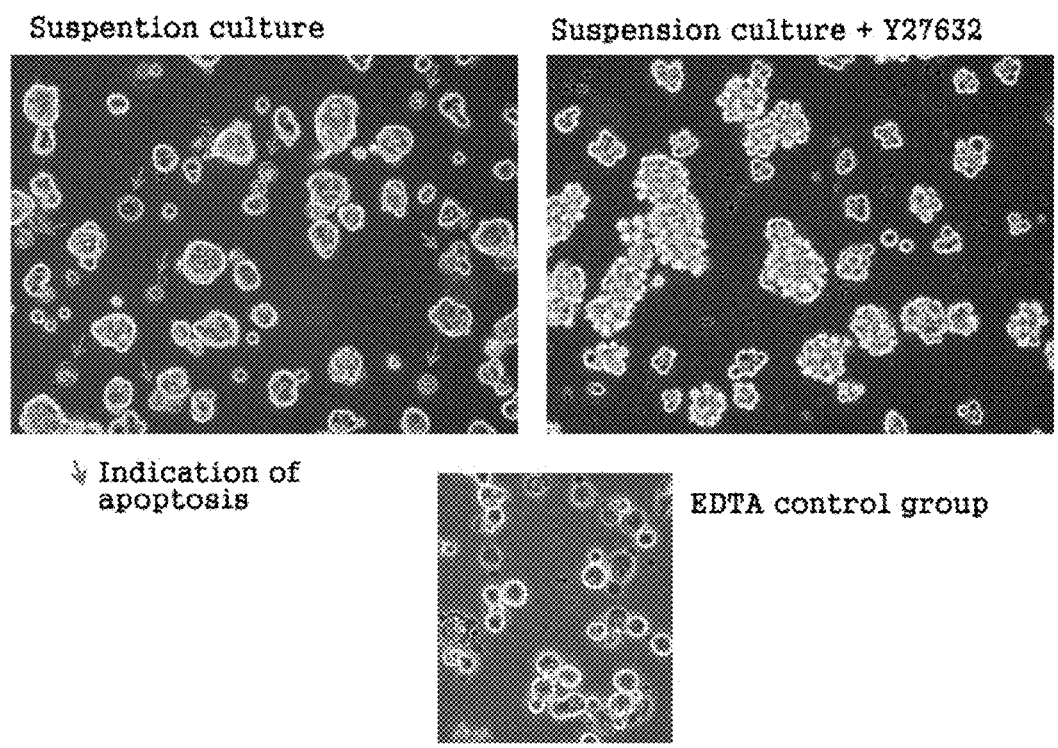
FIG. 2 is a set of photographs (100× magnification) showing the results of trypan blue staining of aggregated cells after 24 hours of culture of Y27632-untreated control cells and Y27632-treated cells. In the Y27632-untreated group, apoptosis was observed in single cells other than aggregated cells. When cells were treated with calcium chelate EDTA, no cell aggregation occurred, and thus apoptosis occurred in all the cells, but when cells were treated with Y27632, apoptosis of non-aggregated single cells was prevented, and thus cell aggregation was further increased.

Control cells cultured in general medium and cells cultured in Y27632-containing medium were counted, and as a result, it was shown that, in the case of the control cells, the number of dead cells among a total of $1.8 \times 10^6$ cells was $1.26 \times 10^6$ and the number of viable cells was $0.54 \times 10^6$ corresponding to a viability of 30%. However, in the case of the cells cultured in the Y27632-containing medium, the number of dead cells among a total of $1.8 \times 10^6$ cells was $0.54 \times 10^6$ and the number of viable cells was $1.26 \times 10^6$ corresponding to a viability of 70%. Such results indicated that the activity of cells during suspension culture was significantly increased by Y27632 (FIGS. 1 and 2).

Western Blotting

Figure 3:
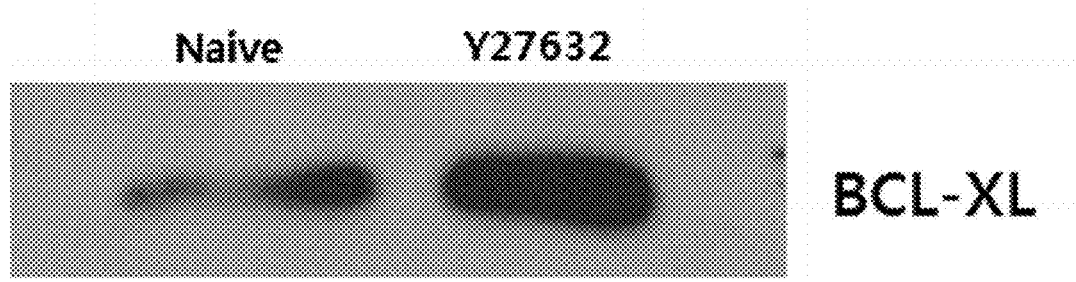
FIG. 3 is an image showing the results of Western blotting performed to examine the expression levels of BCL-XL in Y27632-treated cells and control (naive) cells.
Figure 4:
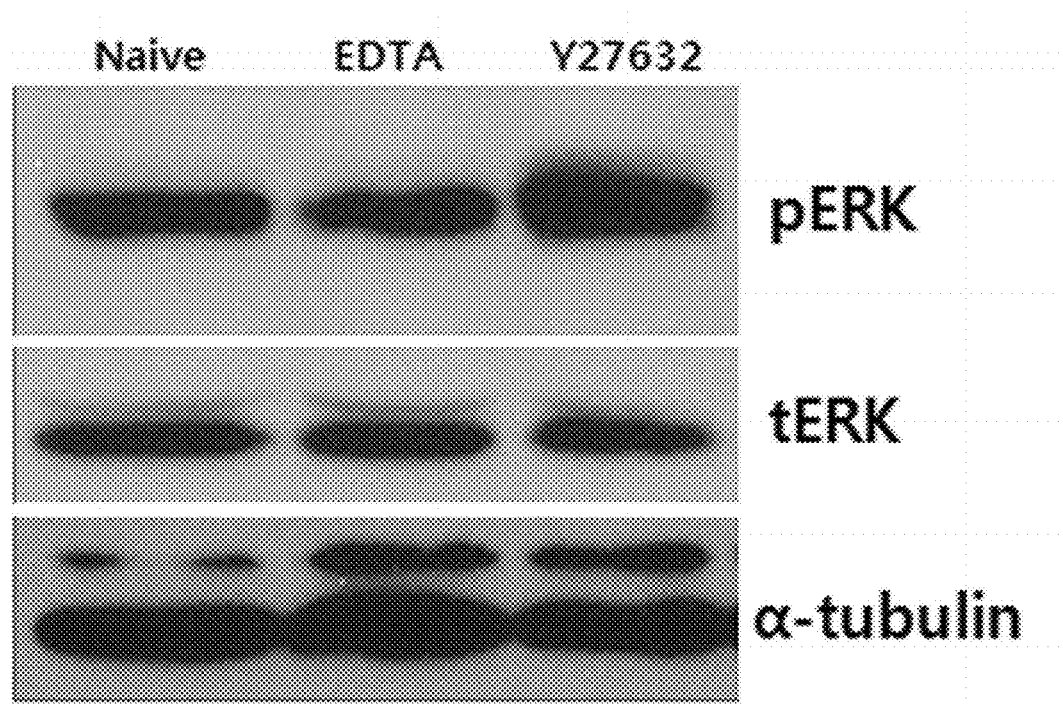
FIG. 4 is an image showing the results of Western blotting performed to examine the degrees of phosphorylation of ERK (extracellular signal-regulated kinase) in Y27632-treated cells and control (naïve) cells.

Western blotting was performed in order to examine changes in the viability and activity of cells at the protein level, and as a result, it was shown that the phosphorylation of ERK (extracellular signal-regulated kinase), which indicates the expression of the anti-apoptosis factor BCL-XL and the activity of cells, significantly increased in Y27632-treated cells (FIGS. 3 and 4).

HGF ELISA

Figure 5:
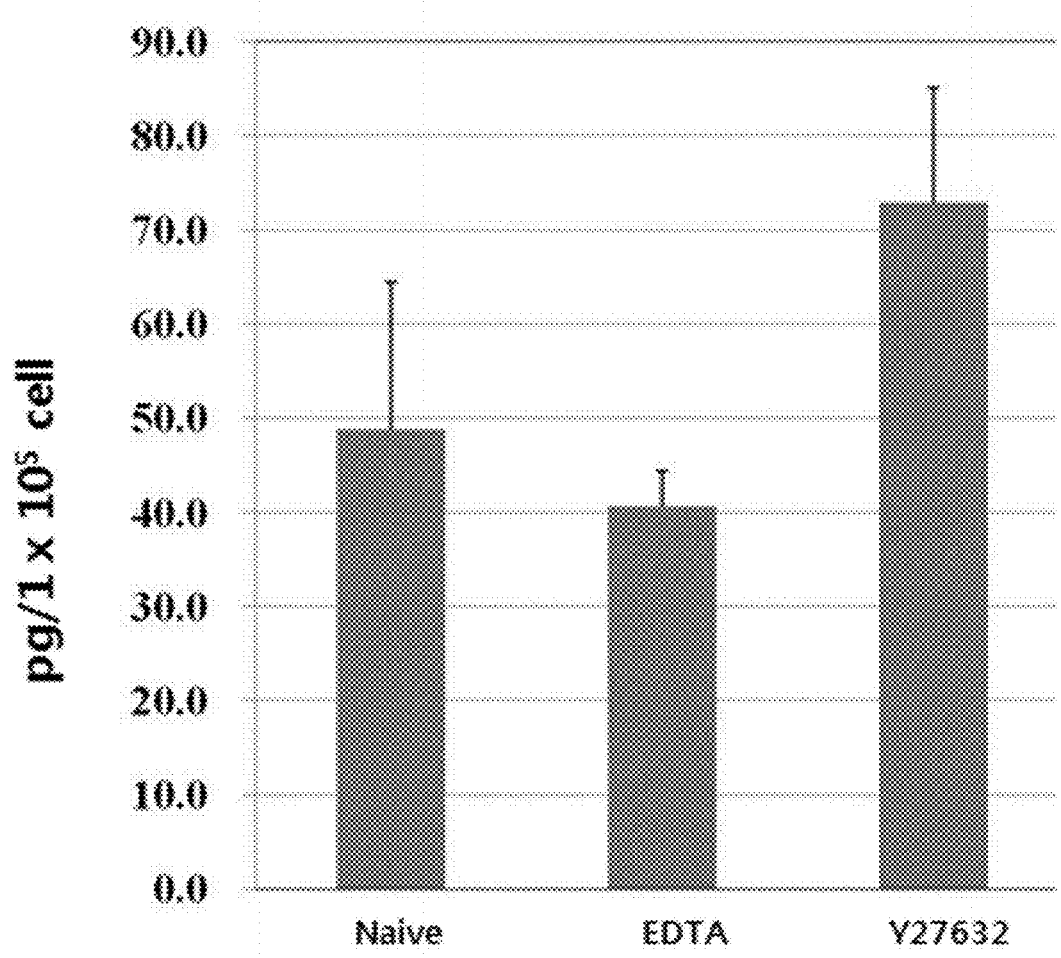
FIG. 5 shows the results of ELISA analysis performed to compare the expression level of HGF between Y27632-treated cells, untreated control cells and EDTA-treated control cells.
Figure 6:
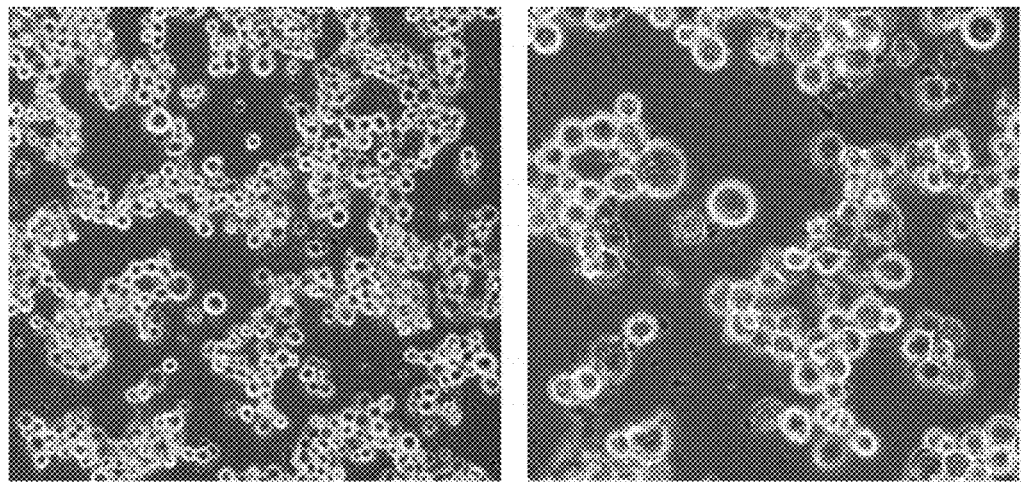
FIG. 6 is a set of photographs taken at 24 hours after suspension culture of mesenchymal stem cells under an anoxic anaerobic condition and shows that the cells are suspended as single cells without aggregation. Left photograph: 40× magnification, and right photograph: 100× magnification.

In order to measure the expression level of the factor HGF in an ischemic anoxic anaerobic condition, ELISA analysis was performed. As a result, it was shown that the expression level of HGF was significantly higher in Y27632-treated cells than in untreated control cells and EDTA-treated control cells (FIG. 5).

Figure 7:
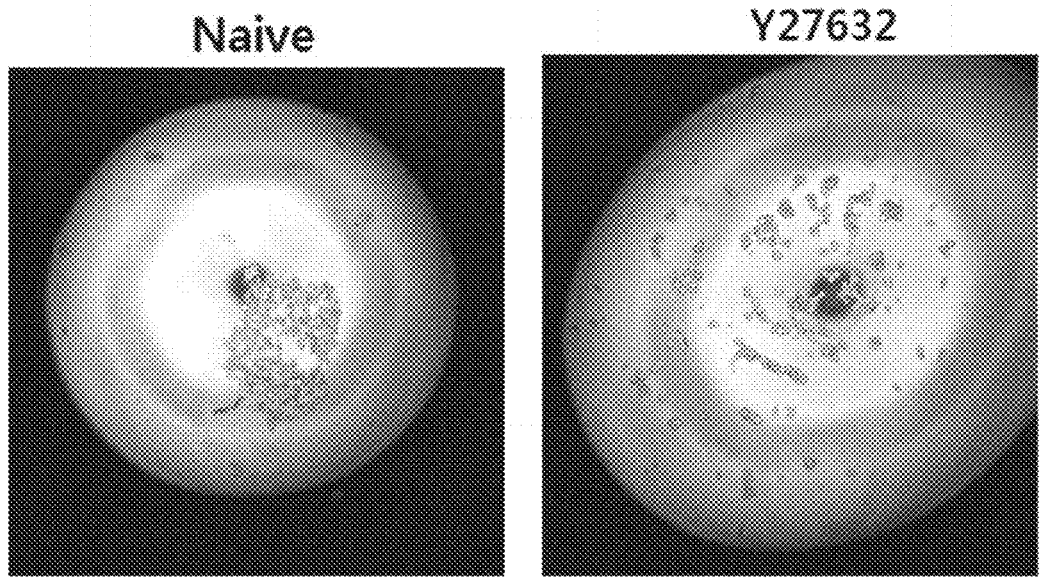
FIG. 7 is a set of photographs (40× magnification) showing the results of comparison of cell viability between Y27632 treatment and non-treatment under an anoxic anaerobic condition. Under the anoxic anaerobic condition, aggregation of mesenchymal stem cells was not observed, and thus a high level of apoptosis occurred in the control group, but the Y27632-treated cells were maintained in a single-cell state while they did not undergo apoptosis.

Culture of human mesenchymal stem cells under anaerobic condition and cell counting Control cells in general medium and cells cultured in Y27632-containing medium under an anaerobic condition for 6 hours were counted. As a result, in the case of the control cells, after 6 hours of culture, the number of dead cells among a total of $1.6 \times 10^6$ cells was $4.0 \times 10^5$, and the number of viable cells was $1.2 \times 10^6$ corresponding to a viability of 75%. However, in the case of the cells cultured in the Y27632-containing medium, the number of dead cells among a total of $1.6 \times 10^6$ cells was $2.4 \times 10^5$, and the number of viable cells was $1.2 \times 10^6$ corresponding to a viability of 84%. Meanwhile, after 24 hours of culture, in the case of the control cells, the number of dead cells among a total of $1.12 \times 10^6$ cells was $6.4 \times 10^5$, and the number of viable cells was $5.2 \times 10^5$ corresponding to a viability of 45%. However, in the case of the cells cultured in the Y27632-containing medium, the number of dead cells among a total of $1.4 \times 10^6$ cells was $1.6 \times 10^5$, and the number of viable cells was $1.24 \times 10^6$ corresponding to a viability of 90%. Such results indicated that the total number of cells was maintained by Y27632 and that the activity of cells was significantly increased due to the proliferation of viable cells (FIG. 7).

Induction of Suspension of Human Mesenchymal Stem Cells (BM-MSC) by Antioxidant

Figure 8A:
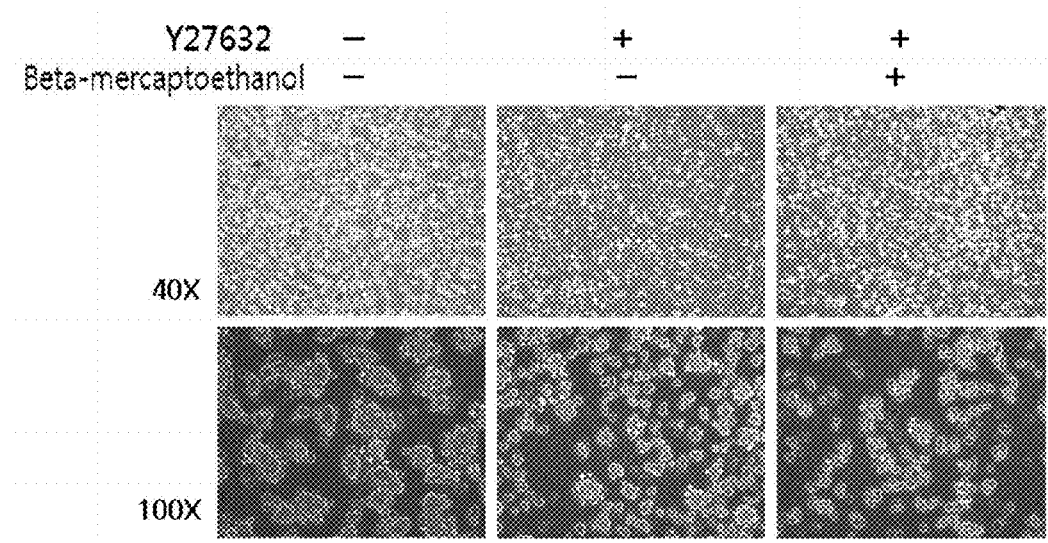
FIG. 8a: 40× and 100× magnifications.
Figure 8B:
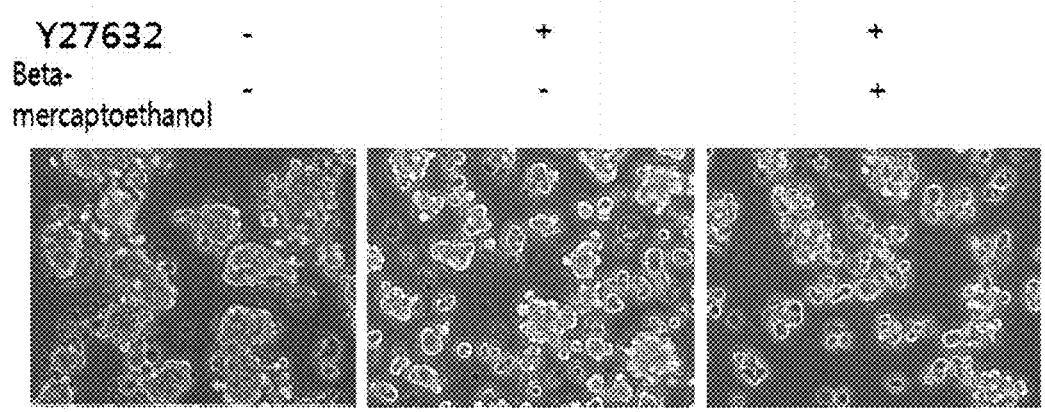
FIG. 8b: 200× magnification.

In order to examine apoptosis inhibition efficiency when cell aggregation is inhibited in an anoxic condition, the activity of cells was observed after culture in the presence or absence of Y27632 and beta-mercaptoethanol. As a result, as shown in FIG. 8, the efficiency with which single cells were cultured greatly increased when Y27632 and beta-mercaptoethanol were added together.

Induction of Suspension Culture of Single Cells Using E-Cadherin Blocker

Figure 9:
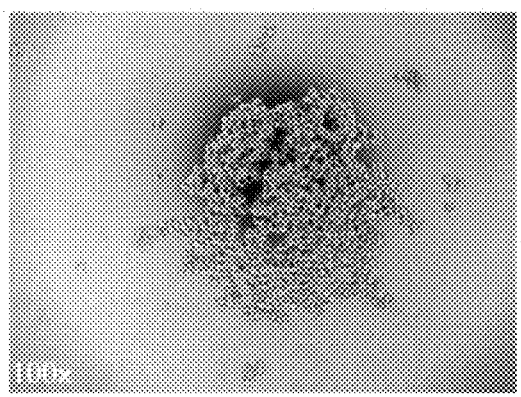
FIG. 9 shows that cell aggregation in suspension culture was inhibited using an E-cadherin blocking antibody and that HGF efficiency was increased by treatment with Y-27632 for 24 hours.
Figure 9:
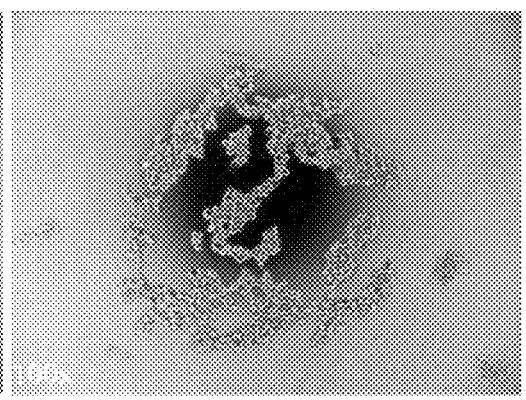
Figure 9:
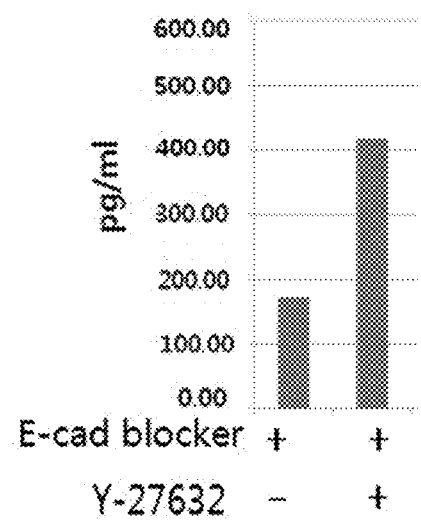

In order to examine an increase in the efficiency of cells when cell aggregation in a suspension condition is inhibited by an E-cadherin blocker, the expression level of HGF was examined. As a result, as shown in FIG. 9, cell aggregation during suspension culture was inhibited by the E-cadherin blocker, and the expression level of the hepatocyte growth factor (HGF) increased.

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

The invention claimed is:

1. A method for inhibiting apoptosis of human mesenchymal stem cells during suspension culture, comprising
   culturing human mesenchymal stem cells; and
   proliferating the human mesenchymal stem cells in a suspension culture under an anoxic anaerobic condition in the presence of a Rho-associated kinase (ROCK) inhibitor under a condition in which aggregation of the stem cells is inhibited,
wherein
   the ROCK inhibitor is a compound represented by the following Formula 1,

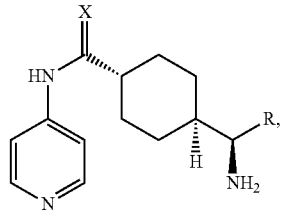

Formula 1 wherein X is oxygen, and R is methyl.

2. The method of claim 1, further comprising an antioxidant.

3. The method of claim 2, wherein the antioxidant is selected from the group consisting of glutathione, cysteine, cysteamine, ubiquinol and bME (beta-mercaptoethanol).

4. The method of claim 1, wherein the proliferation step consists of at least 6 to 24 hours.

* * * * *